(12) United States Patent
Nakanishi et al.

(10) Patent No.: US 6,207,098 B1
(45) Date of Patent: Mar. 27, 2001

(54) METHOD FOR PRODUCING POROUS INORGANIC MATERIALS

(75) Inventors: Kazuki Nakanishi, Shiga; Naohiro Soga, Hyogo; Tokiyo Minakuchi, Kyoto, all of (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/331,478

(22) PCT Filed: Dec. 12, 1997

(86) PCT No.: PCT/EP97/06980

§ 371 Date: Jun. 22, 1999

§ 102(e) Date: Jun. 22, 1999

(87) PCT Pub. No.: WO98/29350

PCT Pub. Date: Jul. 9, 1998

(30) Foreign Application Priority Data

Dec. 26, 1996 (JP) .................................................. 8-347765
Dec. 26, 1996 (JP) .................................................. 8-347772

(51) Int. Cl.$^7$ .................................................. B29C 39/00
(52) U.S. Cl. .................... 264/414; 264/413; 264/415; 264/419; 264/425; 264/426
(58) Field of Search .................... 428/220; 501/12, 501/39; 264/413, 414, 415, 419, 425, 426, 430

(56) References Cited

U.S. PATENT DOCUMENTS 5,009,688 * 4/1991 Nakanishi .............................. 65/18.3
5,624,875 * 4/1997 Nakanishi .............................. 501/39

FOREIGN PATENT DOCUMENTS 0 363 697 * 4/1990 (EP) .
95 03256  2/1995 (WO) .

* cited by examiner

Primary Examiner—Merrick Dixon
(74) Attorney, Agent, or Firm—Millen White Zelano & Branigan (57) ABSTRACT

The present invention relates to a process for producing inorganic porous materials, mainly composed of glass or glass-ceramic components. The glass or glass-ceramic components can have interconnected continuous macropores with a median diameter larger than 0.1 μm, and mesopores in the walls of said macropores, said mesopores having a median diameter between 2 and 100 nm. The process can include dissolving a water-soluble polymer or some other pore forming agent and a precursor for a matrix dissolving agent in a medium for mixing with a metalorganic compound.

17 Claims, 4 Drawing Sheets

METHOD FOR PRODUCING POROUS INORGANIC MATERIALS

This invention relates to an improved method for producing porous inorganic materials. The method of this invention is favorably utilized in manufacture of sorbents for chromatography, fixed phases for thin-layer chromatography, porous materials for blood separation, moisture-absorbing porous materials, porous materials for adsorbing low-molecular materials for deodorization, or porous materials for enzyme carriers.

Porous inorganic materials are favorably applied to producing columns for chromatography, porous filters for separating blood, porous catalysts, or enzyme supports. Such inorganic porous columns can be favorably applied to liquid- and gas-chromatography. These columns can be used unmodified or modified e.g. by covering their surface with molecules like hydrophobic hydrocarbon ligands (e.g. octadecyl ligands) or like hydrophilic ligands like 2,3-dihydroxypropyl derivatives. Other derivatives useful for separations are known in the art. The ligands of such modified columns can be further modified using known procedures. Porous catalysts or enzyme supports can be prepared by binding enzymes, e.g. glucose isomerase, or catalytic metal elements, e.g. platinum and palladium. Such inorganic porous columns can also be attached to an injector or a catheter for blood injection. Due to their mechanical rigidity and heat stability, which allows sterilization by heat, inorganic base materials are preferred.

The sol-gel method is one liquid phase reaction path to produce inorganic porous materials, especially silica gels. The sol-gel method denotes widespread processes in which polymerizable low molecular weight species are first generated, and through polymerization reactions, aggregated or polymerized materials are finally obtained. For example, the sol-gel method can be applied by hydrolyzing metal alkoxides, metal chlorides, metal salts or coordinated compounds which typically contain carboxyl or beta-diketone ligands. A process of this kind is disclosed in Japanese Patent Publication No. 8-29952 and corresponding EP 0 363 697 and U.S. Pat. No. 5,009,688. In this process an organic polymer is used, which is compatible with the solution of the metal alkoxide or its polymer, and which undergoes phase separation during the hydrolysis-polymerization step. This method comprises preparing a gel which has a solvent-rich phase capable of giving macropores of not smaller than about 100 nanometers in size, through sol-gel conversion in the presence of a pore forming agent, and finally drying and calcining the material. The porous inorganic materials produced by this process display connected open macropores. Examples of pore forming agents disclosed in these documents are: sodium polystyrene sulfonate, polyacrylic acid, polyallylamine, polyethylene-imine, polyethylene oxide, and polyvinyl pyrrolidone. Adding lower alkyl alcohols like methanol or ethanol to the gelling mixture can also be used to modify the size of the macropores.

Especially for use in chromatography the porous inorganic material should display another set of pores to enhance the specific surface of the material. These pores have to be accessible for the analyte; therefore mesopores of appropriate size (2 to 100 nm) should be present in the walls of the macropores. A method for manufacturing such porous materials which possess interconnected continuous macropores with a median diameter larger than 0.1 $\mu$m and additional mesopores in the walls of said macropores, said mesopores having a median diameter between 2 and 100 nm has been disclosed in Japanese Patent Application Laid-open No. 7-41374 and corresponding EP 0 710 219 and U.S. Pat. No. 5,624,875. This method comprises preparing a gel which has a solvent-rich phase capable of giving macropores of not smaller than about 100 nanometers in size, through sol-gel conversion in the presence of a pore forming agent, followed by dipping the wet monolithic gel in an aqueous solutions containing a matrix dissolving agent thereby modifying the distribution of mesopores in the gel, and finally drying and calcining the porous inorganic material. Examples of matrix dissolving agents disclosed in these documents are basic substances like sodium hydroxide or aqueous ammonia, or hydrofluoric acid.

Additional disclosure of technical background is found in the documents mentioned above.

Where porous materials are used as carriers for various purposes, it is necessary that they have an optimal median pore diameter and have pore size distribution as narrow as possible. The diameter of their macropores often controls the flow-rate and the pressure drop in the system. The accessibility of the surface of the pores is usually controlled by the diameter of the mesopores. Therefore, for porous materials to be obtained through sol-gel conversion, various attempts have heretofore been made at controlling the reaction conditions for the formation of gel to thereby control the pore size of the porous material to be derived from the gel.

However, as using a water-soluble polymer, this method still causes problems in that the preparation of the reaction system takes much time, and that the characteristics of the product depends on the molecular weight distribution thereof. In addition, since this method comprises separate steps for the formation of the gel and for the solvent substitution thereof, it is a complicated one.

It had been found that further improvements of the porous inorganic materials would be highly needed. Such improvement refer to controling the formation of both the macro- and the mesopores. Such improvements are especially needed where the porous inorganic materials are used as base materials for monolithic columns for chromatography; especially for use in preparative chromatography where larger columns (e.g. diameter typically larger than 1 cm) are needed.

The inventors found improvements related to the manufacture of porous inorganic materials. These improvements comprise using a nonionic surfactant as pore forming agent and novel methods of applying matrix dissolving agents by using precursors of matrix dissolving agents. When the precursor of a matrix dissolving agent that has been dissolved in the gel is reacted to yield the matrix dissolving agent (e.g. by thermolysis, sometimes also called pyrolysis), the gel can easily be converted into a porous material with mesopores of at most about 100 nanometers in inner size and having a narrow pore size distribution. Because the matrix dissolving agent typically is freed from its precursor by thermolysis, a precursor of a matrix dissolving agent can also be called a thermolyzable (sometimes also called pyrolyzable) compound.

The object of the present invention is a process for producing inorganic porous materials, mainly composed of glass or glass-ceramic components, having interconnected continuous macropores with a median diameter larger than 0.1 $\mu$m, and having mesopores in the walls of said macropores, said mesopores having a median diameter between 2 and 100 nm via sol-gel route which includes the steps of:

(a) Dissolving a water-soluble polymer or some other pore forming agent and a precursor for a matrix dissolving agent in a medium that promotes the hydrolysis of the metalorganic compound (see step b);

(b) mixing a metalorganic compound which contains hydrolyzable ligands to promote hydrolysis reaction;

(c) solidifying the mixture through the sol-gel transition, whereby a gel is prepared which has threedimensional interconnected phase domains one rich in solvent the other rich in inorganic component in which surface pores are contained;

(d) setting the matrix dissolving agent free from its precursor, whereby the matrix dissolving agent modifies the structure of said inorganic component;

(e) removing the solution by evaporation drying and/or heat-treatment;

(f) calcining the gel to form the porous material.

In preferred embodiments of the invention silica is the base material of the porous inorganic materials and urea or compounds having an amido group or an alkylamido group are used as precursor of the matrix dissolving agent. Object of the invention are likewise porous inorganic materials obtainable by the process of the invention.

Another object of the invention is the use of non-ionic surfactants as pore forming agent in a process of manufacturing porous inorganic materials. Preferred nonionic surfactants are ether derivatives of polyoxyethylene, especially those containing an alkyl-, aryl-, alkylaryl- (e.g. an alkylphenyl), or arylalkyl (e.g. phenylalkyl) residue.

Further experimental details are given in the examples.

In the present invention the sol-gel method is used to control the pore size of the porous inorganic material; in this method metal compounds having a hydrolyzable functional group like metal alkoxides are used as starting materials with additions of appropriate chemical substances to result in the formation of characteristic phase-separated structure, of which solvent-rich pore forming phase converts to the macropore of the dried gel material. Such starting materials and the conditions necessary to hydrolyse these starting materials are known in the art. Preferred metal alkoxides are silicon alkoxides, which may include, for example, tetramethoxysilane, tetraethoxysilane, methyltrimethoxysilane, ethyltrimethoxysilane and vinyl trimethoxysilane. However, these examples are not limitative. Other suitable metal alkoxides or other suitable metal compounds including mixtures of these compounds are known in the art.

The conditions are chosen so as to hydrolyze the metal compound having a hydrolyzable functional group and to cause polymerization of the metal compound. At the same time the sol-gel transition of the reacting solution and the phase separation into solvent-rich phase and a phase rich in metal compound (skeleton phase) are induced. For silicon alkoxides as metal compound having a hydrolyzable functional group the hydrolysis is done in an acid medium. Diluted organic or inorganic acids are preferred in this case. Especially preferred is the use of acetic acid or nitric acid using concentrations between 1 mmol/l and 2 mol/l. Other acidic media suitable to carry out the hydrolysis of silicon alkoxides are known in the art. Suitable reagents for the hydrolysis of other metalorganic compounds are known in the art as well.

Watersoluble organic polymers such as poly(ethylene oxide) are favorably used as additive chemical substance in the pore forming phase. These substances are collectively called pore forming agents. Other such pore forming agents are known in the art; examples are: sodium polystyrene sulfonate, polyacrylic acid, polyallylamine, polyethyleneimine, polyethylene oxide, and polyvinyl pyrrolidone.

The use of a novel class of pore forming agents is one object of this invention. These novel pore forming agents are non-ionic surfactants. Non-ionic surfactants are basically known. The preferred species of non-ionic surfactants are derivatives of polyethylene oxide wherein the polyethyleneoxide moiety has a degree of polymerization between 5 and 100; especially preferred are such surfactants having a degree of polymerization between 8 and 20 in their polyethyleneoxide moiety. The polyethylene oxide moiety of the non-ionic surfactant is connected to a lipophilic moiety, typically by an ether bridge. However other polyethylene oxide containing surfactants are also known in the art, e.g. long chain fatty acid ester derivatives of polyoxyethylene sorbitanes. Non-ionic surfactants possessing polyoxypropylene residues as hydrophilic moiety, such as polyoxypropylene alkyl ethers can also be used. Preferred polyethylene oxide containing surfactants are those which are derivatized with a lipophilic alkyl group with 8 to 20 C-atoms, or with a lipophilic aryl group which can be substituted with one or several alkyl groups, and which have 6 to 25 C-atoms in total. Examples of the latter group of polyethylene oxide containing surfactants are polyoxyethylene nonylphenyl ether, polyoxyethylene octylphenyl ether, or polyoxyethylene (1,1,3,3-tetramethylbutyl)phenyl ether. However, these examples are not limitative. The hydrophilic lipophilic balance (HLB) system can be used to facilitate to estimate the behavior of non-ionic surfactants, and can be used as guideline for exchanging different nonionic surfactants. The amount of non-ionic surfactant to be added varies, depending on the type of said non-ionic surfactant and also on the type and the amount of the metal alkoxide added, but may be from 1.0 to 10.0 g, preferably from 1.5 to 6.0 g, per 10 g of the metal alkoxide.

The non-ionic surfactant has the function of inducing both sol-gel conversion and phase separation at the same time. While being gelled, the reaction system is separated into a solvent-rich phase and a skeleton phase.

In order to introduce mesopores into the walls of the porous inorganic material Japanese Patent Application Laid-open No. 7-41374 and corresponding EP 0 710 219 and U.S. Pat. No. 5,624,875 disclose the use of matrix dissolving agents, e.g. sodium hydroxide, aqueous ammonia, or hydrofluoric acid. These matrix dissolving agents are used by dipping the polymerized gel into a solution containing the matrix dissolving agent. It had been found that this step can be simplified and improved by using a precursor of a matrix dissolving agent The matrix dissolving agent is freed from its precursor by thermolysis, or by catalytic or enzymatic action. One example of a precursor of matrix dissolving agents is urea, which gives yield to ammonia; this precursor is especially useful, when the matrix is based on silica. Additional examples include organic amides such as formamide, N-methylformamide, N,N,-dimethylformamide, acetamide, N-methylacetamide, and N,N-dimethylacetamide, which also give yield to ammonia. However, as will be mentioned in the examples to follow hereinunder, the precursor of the matrix dissolving agent is not limited to these, but may be any one capable of making the solvent basic after thermolysis, since in the case of using silica as skeleton material the pH value of the solvent after thermolysis is an important factor in the method of the present invention. In addition, those capable of producing a compound having the property of dissolving silica, such as hydrofluoric acid, through thermolysis are also usable in the present invention.

The amount of the thermolyzable compound to be in the reaction system of the present invention may vary, depending on the type of said compound. For urea, for example, its amount may be from 0.1 to 3 g, preferably from 0.2 to 2 g, per 10 g of the reaction system. The heating temperature for the thermolysis of urea may fall between 60° C. and 200° C. In the thermolyzing step, it is effective to put the gel in a closed container in order to make the vapor pressure of the thermolyzed product saturated and to rapidly make the solvent have a steady pH-value. After the thermolysis, the pH of the solvent is preferably from 9.0 to 11.0. The time after which the pore structure of the gel stays substantially unchanged under the processing conditions depends on the type precursor for the matrix dissolving agent and on the conditions applied (e.g. the temperature); when urea is used as the precursor for the matrix dissolving agent the necessary time typically is between 3 hours (e.g. at 200° C.) and 30 days (e.g. at 60° C.).

One means of the present invention to attain said object is characterized by previously dissolving a thermolyzable compound in a reaction solution, forming, from said reaction solution through its sol-gel conversion, a gel that comprises a solvent-rich phase containing three-dimensionally networked open pores having a mean pore diameter of not smaller than 100 nanometers and an inorganic substance-rich skeleton phase containing particles each having mesopores on its surface, then heating the wet gel to thermolyze said thermolyzable compound existing in the reaction system, and thereafter drying and heating the gel.

In one method of the present invention, where a non-ionic surfactant and a precursor of a matrix dissolving agent are dissolved in an aqueous acidic solution and a metal compound having a hydrolyzable functional group is added thereto to thereby hydrolyze said metal compound, formed is a gel comprising a solvent-rich phase and a skeleton phase as separated from each other. After the product (gel) is solidified and then ripened for a suitable period of time, the wet gel is heated, whereby the matrix dissolving agent is freed from its precursor, which has been previously dissolved in the reaction system, resulting in the increase in the pH of the solvent that is kept in direct contact with the inner walls of particles constituting the skeleton phase. As a result, the solvent corrodes said inner wall to thereby change the inner surface of said inner wall into a roughened one, whereby the pore size of said particles is gradually enlarged.

For the gel consisting essentially of silica, the degree of said change in an acidic or neutral region will be very small, but with the increase in the thermolysis to increase the pH of the aqueous solution, the part constituting each pore is dissolved and re-precipitated to give a more flat part, thereby inducing more active reaction to enlarge the mean pore size of the mesopores.

If the gel has only fine and three-dimensionally restrained pores without having any macropores, even its part capable of being dissolved under equilibrated conditions could not produce a dissolved substance capable of being diffused into the external solution, so that the original fine pore structure will remain in the gel to have a relatively large proportion. As opposed to this, if the gel has a solvent rich-phase capable of giving macropores, it contains a large amount of only two-dimensionally restrained fine pores, so that the exchange of substances between said solvent-rich phase and the external aqueous solution may be effected well frequently in the gel, resulting in the removal of fine pores with the growth of macropores in the gel while preventing the entire pore size distribution of the resulting gel from being broadened.

The pore size of macropores and their corresponding specific surface are determined using mercury porosimetry. It is also possible to estimate the pore dimensions from scanning electron micrographs (SEM). The pore size of mesopores and their specific surface are determined using nitrogen adsorption (BET-method). Measurements followed standard protocols.

The porous inorganic materials of this invention possess macropores larger than 0.1 $\mu$m, typically from 0.3 up to 10 or 20 $\mu$m (median values; centre point of distribution curve). Mesopores of these materials, which can be introduced using matrix dissolving agents or their precursors are between 2 and 100 nm, typically between 4 and 60 nm (median values; centre point of distribution curve).

The final preparation steps for the manufacture of the porous inorganic materials according to the present invention include an optional rinsing step, e.g. with water, a drying step, and a calcining step. Typically drying is achieved at temperatures between 20 and 80° C.; this step can be facilitated using an oven with air circulation or by applying reduced pressure. Calcining typically is done at final temperatures between 400 and 900° C. for one to several hours. The final temperature is reached using a temperature programme, typically rising the temperature between 50 and 200° C. per hour.

If the porous inorganic materials according to the present invention are used as sorbents for chromatographic separations, they are usually derivatized in order to allow different mechanisms of separations. Methods for such derivatizations and the use of such derivatized separating materials are known in the art applicable information about derivatization of particulate silica materials is contained in handbooks like "Porous Silica" (K. K. Unger, ed., (1979)

Elsevier Scientific Publishing Company). The groups which are introduced into the base material in order to allow chromatographic separations can be summarized as separation effectors. Examples for different modes of chromatographic separations are ion exchange chromatography, reversed phase chromatography, hydrophobic interaction chromatography, affinity chromatography, chiral separations. Dependent on these modes of action different separation effectors can be used: ionic groups like —COOH, —$SO_3H$, —$N(C_2H_5)_2$, or —$N^+(C_2H_5)_3$, hydrophobic groups like $C_{18}$- or $C_8$-alkyl or phenyl or butyl, affinity ligands like antibodies or enzyme subtrates (or substrate analogues), chiral ligands like aminoacid derivatives or polysaccharide derivatives. Additional examples and more details of such separation effectors are given in PCT/EP97/03 601.

This invention has been made on the basis of these findings, and porous inorganic materials manufactured by the improved processes show narrow pore size distributions and have pore structures with a desired center pore diameter and a narrow pore size distribution. It was found that these features can be attained with good reproducibility.

As has been described hereinabove, according to the present invention, porous materials having a pore size distribution as controlled to fall within a described range can be produced. In addition, since the porous materials produced according to the present invention have a double-pore structure comprising macropores and mesopores, they can be used not only in manufacture of fillers for particles-filled columns but also in other applications of producing monolithic columns made of only said porous materials. In particular, since the method of the present invention uses a non-ionic surfactant, the volume of the mesopores to be formed can be well controlled to be up to about 2.0 $cm^3/g$ with high reproducibility.

The improvements disclosed in this application allow to prepare porous inorganic materials with improved mechanical stability, especially when dimensions of such articles are larger than one centimeter. They allow further to prepare porous inorganic materials with a higher volume of mesopores. Typically using prior art processes materials with about 1 $cm^3/g$ can be prepared.

Without further elaboration, it is believed that one skilled in the art can, using the preceding description, utilize the present invention to its fullest extent. The preferred specific embodiments are, therefore, to construed as merely illustrative, and not limitative of the disclosure in any way whatsoever.

The entire disclosures of all applications, patents, and publications cited above and below, and of corresponding applications Japanese hei-8-347765, filed Dec. 26, 1996, and Japanese hei-8-347772, filed Dec. 26, 1996, are hereby incorporated by reference.

EXAMPLES

Example 1

First, 1.00 g of a nonionic surfactant, polyoxyethylene nonylphenyl ether (its oxyethylene moiety has a mean degree of polymerization of 70; produced by Nippon Oils & Fats Co.; hereinafter referred to as NS270) was dissolved in 10.0 g of aqueous solution of nitric acid (1 mol/liter). To the resulting uniform solution, added was 5.15 g of tetramethoxysilane with stirring, and hydrolyzed. After having been stirred for a few minutes, the resulting transparent solution was transferred into a closable container, which was then closed and kept in a thermostat tank at 40° C. After about 170 minutes, the solution became cloudy and then solidified.

The thus-solidified sample was then ripened for a few hours, and thereafter the solvent was evaporated out therefrom at 60° C. Next, the sample was heated up to 600° C. at a heating rate of 100° C./h. Thus was obtained a porous material of amorphous silica.

Figure 1:
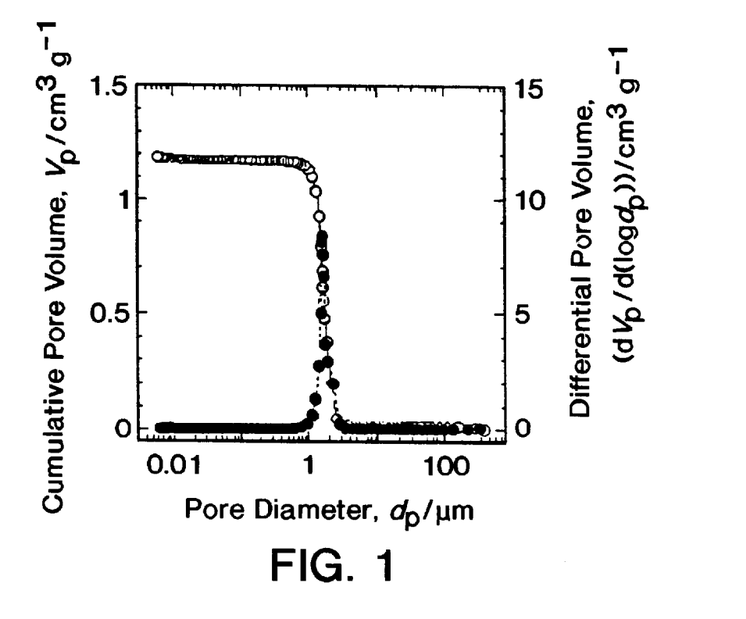
FIG. 1 shows a pore distribution curve of the porous material obtained in Example 1. In this, white spots indicate the cumulative pore volume, and the black spots indicate the differential pore volume.

As a result of its electromicroscopy and mercury penetration, the thus-obtained porous material was verified to have a three-dimensional network structure comprising uniform through-holes having a center pore diameter of about 2 $\mu$m (=2000 nm) and gel skeletons having a thickness of about 1 $\mu$m as entangled together with said through-holes. The pore size distribution in this material is shown in FIG. 1. As a result of its nitrogen adsorption, this material was further verified to have many fine pores of not larger than 3 nm in diameter on the inner walls of said through-holes and have a specific surface area of not smaller than 400 $m^2/g$.

Example 2

In the same manner as in Example 1, except that the amount of the starting NS270 was varied within the range between 0.70 g and 1.20 g various gels were prepared. When the amount of said NS270 was from 1.00 to 1.10 g, the gels obtained were found to have a three-dimensional network structure comprising uniform through-holes having a center pore diameter of about 3 $\mu$m (=3000 nm) and gel skeletons having a thickness of about 1 $\mu$m as entangled together with said through-holes. However, the larger or smaller amount of NS270 used over or below said range resulted in the decrease in the center pore diameter of the through-holes formed, with the result that 0.70 g or 1.20 g of NS270 added gave through-holes of about 0.5 $\mu$m in diameter.

Example 3

In the same manner as in Example 1, except that the temperature for the solidification was varied to 30, 50 or 60° C., various gels were prepared. At 30° C., the gel obtained was a microscopically non-uniform one; and at 50° C. and 60° C., the gels obtained has no through-holes of not smaller than 0.1 $\mu$m in diameter.

The compositions capable of giving gels having open through-holes, like in Example 1, at varying temperature are as follows:

At a temperature of 30° C.; from 0.70 to 1.80 g of NS270, and from 8.4 to 12.0 g of aqueous nitric acid solution of 1 mol/liter, both per 5.15 g of tetramethoxysilane.

At a temperature of 50° C.; from 0.80 to 1.40 g of NS270, and from 10.24 to 12.4 g of aqueous nitric acid solution of 1 mol/liter, both per 5.15 g of tetramethoxysilane.

At a temperature of 60° C.; from 1.00 to 1.35 g of NS270, and from 12.0 to 15.2 g of aqueous nitric acid solution of 1 mol/liter, both per 5.15 g of tetramethoxysilane.

Example 4

The process of Example 1, where the degree of polymerization of the oxyethylene moiety in the nonionic surfactant is about 70, was repeated using nonionic surfactants with shorter oxyethylene moieties. Starting compositions capable of giving gels having open through-holes at 40° C., like in Example 1, are as follows:

For NS240 (having a mean degree of polymerization of 40 in its oxyethylene moiety); from 1.00 to 1.60 g of NS240, and from 10.0 to 12.4 g of aqueous nitric acid solution of 1 mol/liter, both per 5.15 g of tetramethoxysilane.

For NS220 (having a mean degree of polymerization of 20 in its oxyethylene moiety); from 1.00 to 1.80 g of NS220, and 9.28 to 10.80 g of aqueous nitric acid solution of 1 mol/liter, both per 5.15 g of tetramethoxysilane.

For NS210 (having a mean degree of polymerization of 10 in its oxyethylene moiety); from 1.20 to 3.00 g of NS210, and from 10.80 to 12.4 g of aqueous nitric acid solution of 1 mol/liter, both per 5.15 g of tetramethoxysilane.

For NS208.5 (having a mean degree of polymerization of 8.5 in its oxyethylene moiety); from 1.20 to 3.00 g of NS208.5, and from 10.8 to 11.6 g of aqueous nitric acid solution of 1 mol/liter, both per 5.15 g of tetramethoxysilane.

Example 5

In the process of Example 1 the nonionic surfactant NS270 was replaced by the nonionic surfactant P210 (polyoxyethylene octylphenyl ether; having a mean degree of polymerization of 10 in its oxyethylene moiety; produced by Nippon Oils & Fats Co.), having a shorter alkyl chain than the nonionic surfactant NS270. The starting compositions capable of giving gels having open through-holes were shifted to those producing a slightly smaller solvent phase at 40° C. Using these starting compositions, obtained were gels having almost the same structure as in Example 1.

Example 6

First, 0.90 g of a water-soluble polymer, polyethylene oxide (produced by Aldrich, product number 85, 645-2) and 0.45 g of urea were dissolved in 10.0 g of aqueous solution of 0.01 N acetic acid. 5 ml of tetramethoxysilane were added to the resulting solution with stirring and were hydrolyzed. After having been stirred for a few minutes, the resulting transparent solution was transferred into a closable container, which was then closed and kept in a thermostat tank at 40° C. After about 40 minutes, the solution became cloudy and then solidified.

The thus-solidified sample was then ripened for a few hours, and thereafter kept at 80° C. in a closed condition for 7 days. The pH of the solvent existing around the gel was about 9. Then the resulting gel was dried at 60° C., and then heated up to 600° C. at a heating rate of 100° C./h. Thus was obtained a porous material of amorphous silica.

Figure 5:
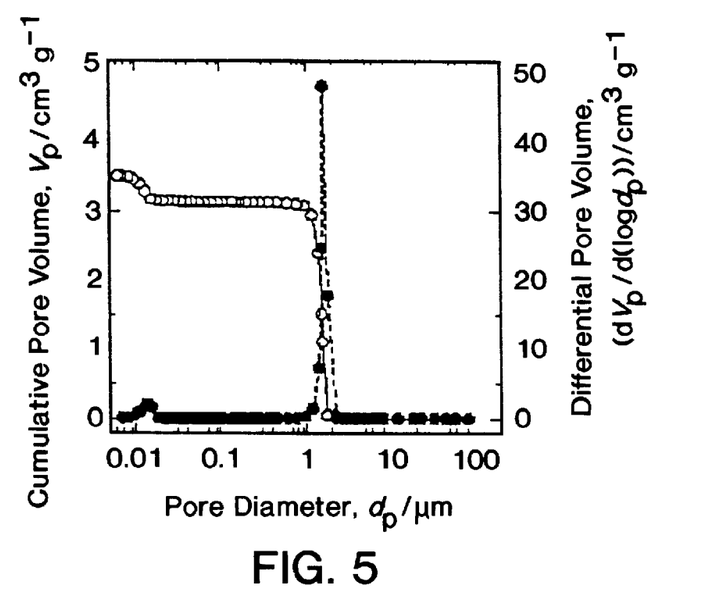
FIG. 5 shows a pore distribution curve of the porous material obtained in Example 6. In this, white spots indicate the cumulative pore volume, and the black spots indicate the differential pore volume.
Figure 6:
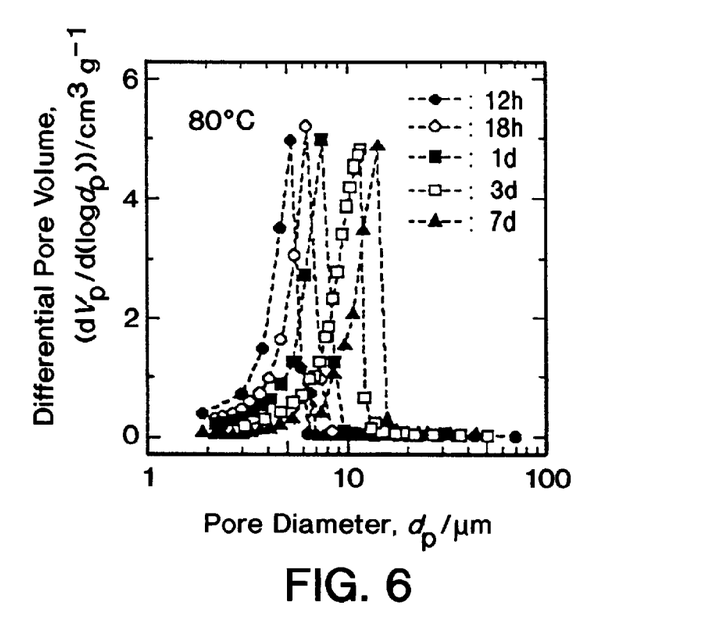
FIG. 6 shows a pore size distribution in various gels obtained herein, for which 0.45 g of urea was used to prepare the gels, and the gels were heated for varying periods of time, and thereafter dried and further heated.

As a result of its electromicroscopy and mercury penetration, the thus-obtained porous material was verified to have a three-dimensional network structure comprising uniform through-holes having a center pore diameter of about 1.6 μm (=1600 nm) and entangled together. The pore size distribution in this material is shown in FIG. 5. As a result of its nitrogen adsorption, this material was further verified to have many fine pores of about 15 nm in diameter on the inner walls of said through-holes. The time for heating the ripened sample in the closed conditions was varied within the range between 3 hours and 7 days, and the differential pore size distribution in each of the thus-heated samples was obtained through nitrogen adsorption, and is shown in FIG. 6.

Figure 7:
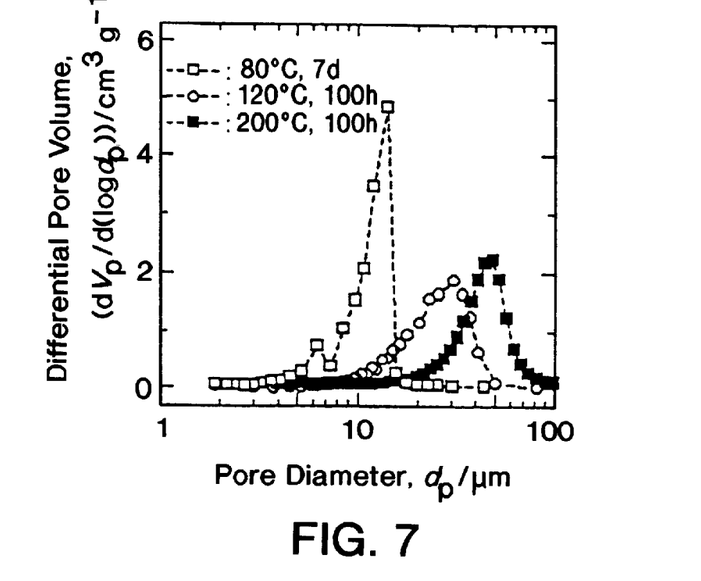
FIG. 7 shows a pore size distribution in various gels obtained herein, for which 0.45 g of urea was used to prepare the gels, and the gels were heated at 80° C., 120° C. or 200° C. for 7 days, and thereafter dried and further heat-treated.

In the same manner as above, except that the temperature in the closed condition was varied to 120° C. or 200° C., porous samples were prepared. In these, the pore distribution of the through-holes was the same as above, but the center pore diameter as measured according to nitrogen adsorption was varied to about 25 nm (at 120° C.) or about 50 nm (at 200° C.). The pore size distribution in each sample, relative to the heating temperature as the parameter, is shown in FIG. 7. This verifies that the higher temperatures for forming the gels produce larger center pore diameters.

Example 7

In the same manner as in Example 6, except that the amount of urea was 0.90 g and that the pH value of the solvent existing around the gel was 10.7, porous materials were prepared.

Figure 8:
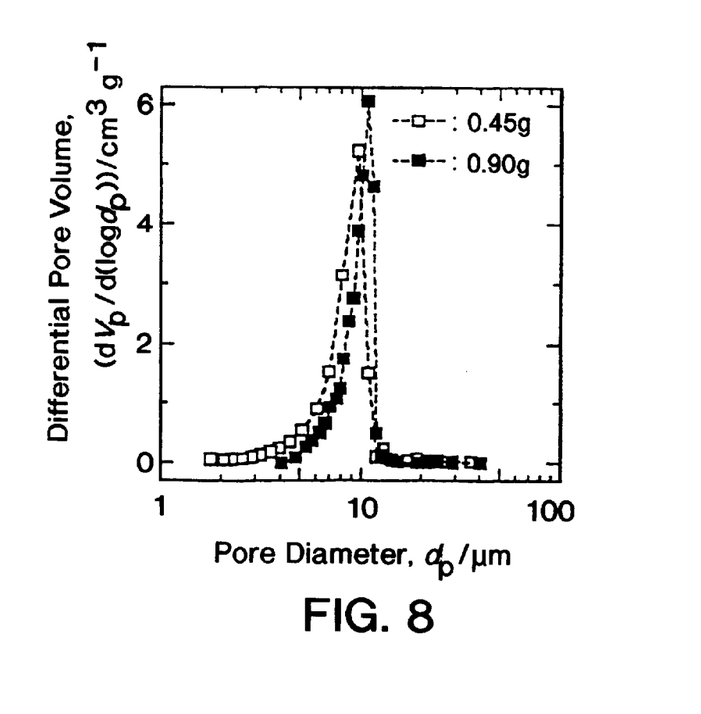
FIG. 8 shows a pore size distribution in various gels obtained herein, for which 0.45 g or 0.90 g of urea was used to prepare the gels, and the gels were heated for 7 days, and thereafter dried and further heat-treated.

In the gels as prepared by heating at 80° C., 120° C. and 200° C., the center pore diameter was 15 nm, 25 nm and 50 nm, respectively, These data correspond well to those in Example 6 within the experimental error, almost not depending on the concentration of urea used. However, the pore size distribution to be derived from the differential distribution curve was smaller in the gels obtained herein than that in those obtained in Example 6. The pore size distribution in each sample, relative to the heating temperature as the parameter, is shown in FIG. 8. This verifies that the higher concentrations of urea added produce a narrower pore size distribution, while producing a larger pore size capacity.

Example 8

In the same manner as in Example 1, except that 0.50 g of urea was added to the starting composition, a gel was prepared. In this case, the gelling time was shortened to about 80 minutes. The solidified sample was further ripened for a few hours, and then kept at 80° C. in a closed condition for varying periods of time. Thereafter the solvent was evaporated out from the sample at 60° C., and then the product was heated up to 600° C. at a heating rate of 100° C./h.

Figure 2:
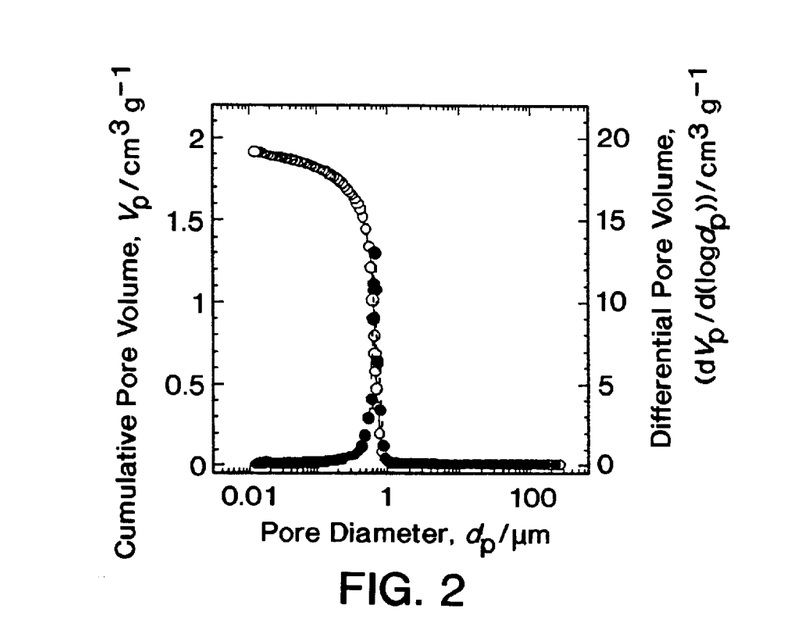
FIG. 2 shows a pore size distribution of open throughholes (macropores) in the gel as obtained in Example 8, in which 0.50 g of urea was used to prepare the gel, and the gel was heated at 80° C., and thereafter dried and further heat-treated.
Figure 3:
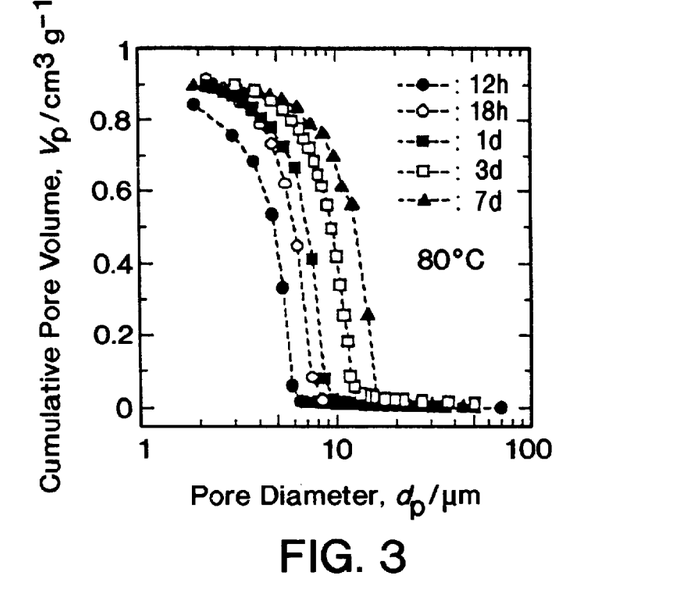
FIG. 3 shows a cumulative pore size distribution in the mesopore region of the gel as obtained in Example 8, in which 0.50 g of urea was used to prepare the gel, and the gel was heated at 80° C., and thereafter dried and further heat-treated.

As a result of its electromicroscopy and mercury penetration, the thus-obtained porous material was verified to have a three-dimensional network structure comprising uniform through-holes having a center pore diameter of about 1 μm (=1000 nm) and gel skeletons having a thickness of about 1 μm as entangled together with said through-holes. The pore size distribution in this material is shown in FIG. 2. As a result of its nitrogen adsorption, this material was further verified to have many fine mesopores of from 5 to 12 nm in diameter on the inner walls of said through-holes, while giving a narrow mesopore distribution, and have a specific surface area of not smaller than 400 m$^2$/g. The cumulative pore capacity of the mesopores was about 1 cm$^3$/g, almost irrespective of the starting compositions used for forming gels. FIG. 3 shows a differential pore size distribution of mesopore regions in the gels as obtained by processing for varying periods of time at 80° C.

In the same manner as above, except that the temperature in the closed condition was varied to 120° C. or 200° C., porous samples were prepared. In these, the pore distribution of the through-holes was the same as above, but the largest center pore diameter as measured according to nitrogen adsorption was varied to about 25 nm (at 120° C.) or about 50 nm (at 200° C.). This verifies that the higher temperatures for forming the gels produce larger center pore diameters.

Example 9

Figure 4:
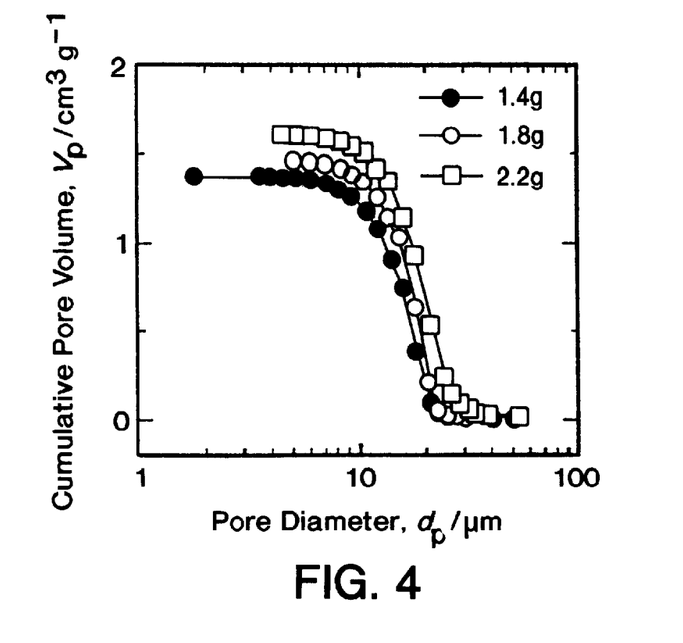
FIG. 4 shows a cumulative pore size distribution in the mesopore regions of the gel as obtained in Example 9, in which 0.50 g of urea and from 1.40 to 1.80 g of the nonionic surfactant NS210 (a polyethylene nonylphenyl ether, the oxyethylene moiety of which has a mean degree of polymerization of 10; produced by Nippon Oils & Fats Co) were used to prepare the gels, and the gels were dried and heat-treated.

The same process as in Example 5, except that NS210 was used as the nonionic surfactant, produced mesopores having the same center pore diameter distribution as in Example 5. In this, however, the cumulative pore capacity varied, depending on the variation in the amount of the nonionic surfactant in the starting composition. Precisely, where the amount of NS210 was varied within the range between 1.40 g and 1.80 g, relative to 5.15 g of tetramethoxysilane and 10.0 g of aqueous nitric acid solution of 1 mol/liter, the cumulative pore capacity was varied within the range between 1.2 and 1.6 cm$^3$/g. FIG. 4 shows the cumulativ pore size distribution of the mesopores in the gels as obtained from various compositions each comprising a varying concentration of NS210. This verifies that the pore capacity of the mesopores in gels can be controlled by suitably selecting the type and the amount of the nonionic surfactant to be used.

What is claimed is:

1. A process for producing inorganic porous materials, mainly composed of glass or glass-ceramic components, having interconnected continuous macropores with a median diameter larger than 0.1 μm, and having mesopores in the walls of said macropores, said mesopores having a median diameter between 2 and 100 nm, via a sol-gel transition route comprising:

(a) dissolving a water-soluble polymer or some other pore forming agent and a precursor for a matrix dissolving agent in a medium that promotes the hydrolysis of metalorganic compounds;

(b) mixing a metalorganic compound which contains hydrolyzable ligands in the medium to promote a hydrolysis reaction thereof;

(c) solidifying the mixture through the sol-gel transition, whereby a gel is prepared which has three-dimensional interconnected phase domains, one rich in solvent and the other rich in an inorganic component in which surface pores are contained;

(d) setting the matrix dissolving agent free from its precursor, whereby the matrix dissolving agent modifies the structure of said inorganic component;

(e) removing the phase rich in solvent by evaporation drying and/or heat-treatment; and (f) calcining the gel to form the porous material.

2. A process as claimed in claim 1, wherein said inorganic component is silica and said precursor of the matrix dissolving agent is urea.

3. A process as claimed in claim 1, wherein said inorganic component is silica and said precursor of the matrix dissolving agent is a compound having an amido group or an alkylamido group.

4. A process as claimed in claim 1, wherein the pore forming agent is a neutral surfactant.

5. Inorganic porous material, mainly composed of glass or glass-ceramic components, having interconnected continuous macropores with a median diameter larger than 0.1 μm, and having mesopores in the walls of said macropores, said mesopores having a median diameter between 2 and 100 nm, obtainable by claim 1.

6. A process for producing inorganic porous materials, mainly composed of glass or glass-ceramic components, having interconnected continuous macropores with a median diameter larger than 0.1 μm, via sol-gel transition route comprising:

(a) dissolving a neutral surfactant in a medium that promotes the hydrolysis of metalorganic compounds;

(b) mixing a metalorganic compound which contains hydrolyzable ligands in the medium to promote a hydrolysis reaction thereof;

(c) solidifying the mixture through the sol-gel transition, whereby a gel is prepared which has three-dimensional interconnected phase domains, one rich in solvent and the other rich in an inorganic component in which surface pores are contained;

(d) immersing the gel in a matrix dissolving agent or a precursor thereof, which can dissolve said inorganic component to introduce mesopores into the walls of said macropores, said mesopores having a median diameter between 2 and 100 nm;

(d) removing the phase rich in solvent by evaporation drying and/or heat-treatment;

(e) calcining the gel to form the porous material.

7. A process as claimed in claim 6, wherein said nonionic surfactant comprises a hydrophilic moiety such as polyoxyethylene and a hydrophobic moiety being an alkyl, an aryl, an alkylaryl, or an arylalkyl group.

8. A process as claimed in one of the claims 6 or 7, wherein said nonionic surfactant is any of polyoxyethylene nonylphenyl ether or polyoxyethylene octylphenyl ether.

9. Inorganic porous material, mainly composed of glass or glass-ceramic components, having interconnected continuous macropores with a median diameter larger than 0.1 μm, obtainable by claim 6.

10. A process according to claim 6 wherein the nonionic surfactant is polyoxyethylene (1,1,3,3-tetramethylbutyl)-phenyl ether.

11. A process according to claim 1 wherein the metalorganic compound is a silicon alkoxide.

12. A process according to claim 1 wherein the metalorganic compound is tetramethoxysilane, tetraethoxysilane, methyltrimethoxysilane, ethyltrimethoxy silane or vinyl trimethoxysilane.

13. A process according to claim 1 wherein the water-soluble polymer or pore forming agent comprises a polyethyleneoxide moiety, a polyoxyethylene sorbitane moiety, or a polyoxypropylene alkylether moiety.

14. A process according to claim 3, wherein the precursor of the matrix dissolving agent is formamide, N-methylformamide, N,N-dimethylformamide, acetamide, N-methylacetamide, or N,N-dimethylacetamide.

15. A process for producing inorganic porous materials, mainly composed of glass or glass-ceramic components, having interconnected continuous macropores with a median diameter larger than 0.1 μm, and having mesopores in the walls of said macropores, said mesopores having a median diameter between 2 and 100 nm, via a sol-gel transition route comprising dissolving a water-soluble polymer or some other pore forming agent and a precursor for a matrix dissolving agent in a medium for mixing with a metalorganic compound.

16. A chromatography column, a porous filter, a porous catalyst, or an enzyme support comprising an inorganic porous material made according to claim 1.

17. A chromatography column, a porous filter, a porous catalyst, or an enzyme support comprising an inorganic porous material made according to claim 6.

* * * * *

UNITED STATES PATENT AND TRADEMARK OFFICE
CERTIFICATE OF CORRECTION

PATENT NO. : 6,207,098 B1  
DATED : March 27, 2001  
INVENTOR(S) : Kazuki Nakanishi et al.

Page 1 of 1

It is certified that error appears in the above-identified patent and that said Letters Patent is hereby corrected as shown below:

<u>Column 12, claim 6,</u>  
Line 16, reads "(d)" should read -- (c1) --

Signed and Sealed this

Ninth Day of April, 2002

Attest:

Attesting Officer

JAMES E. ROGAN  
Director of the United States Patent and Trademark Office